United States Patent [19]

Shiraishi et al.

[11] Patent Number: 5,693,313
[45] Date of Patent: Dec. 2, 1997

[54] TEETH COATING LIQUID

[75] Inventors: Katsuhiko Shiraishi, Fujioka; Kiyokazu Sakurai, Saitama; Tetsuo Kosaka; Takashi Umeno, both of Sawa-gun; Tomoko Hasegawa, Maebashi; Kazuhiro Ami, Fujioka, all of Japan

[73] Assignees: Mitsubishi Pencil Kabushiki Kaisha; Hanix Co., Ltd., both of Tokyo, Japan

[21] Appl. No.: 567,025

[22] Filed: Dec. 4, 1995

[30] Foreign Application Priority Data

Dec. 13, 1994 [JP] Japan .............. HEI 6-332181
Aug. 2, 1995 [JP] Japan .............. HEI 7-215487
Oct. 4, 1995 [JP] Japan .............. HEI 7-257350

[51] Int. Cl.⁶ .............. C09D 5/00; A61K 31/78; A61C 13/00
[52] U.S. Cl. .............. 424/49; 523/115
[58] Field of Search .............. 523/115; 424/49

[56] References Cited

U.S. PATENT DOCUMENTS 5,380,772 1/1995 Hasegawa et al. .............. 522/14
5,489,625 2/1996 Moriwaki et al. .............. 523/118

FOREIGN PATENT DOCUMENTS

Hei 4-82821 3/1992 Japan.
Hei 5-58844 3/1993 Japan.

*Primary Examiner*—Peter F. Kulkosky
*Attorney, Agent, or Firm*—Darby & Darby

[57] ABSTRACT

The present invention provides a teeth-coating liquid comprising a color pigment represented by titanium oxide and a pearl pigment or an extender pigment represented by tricalcium phosphate, dispersed singly or in combination thereof in an alcohol series solvent, mainly ethanol with an N-methacryloylethyl-N,N-dimethylammonium.α-N-methylcarboxybetaine.butyl methacrylate copolymer, and an applicator for the coating liquid described above.

This teeth-coating liquid provides excellent dispersion stability, gloss, coating property and sticking performance by using the N-methacryloylethyl-N,N-dimethylammonium.α-N-methylcarboxybetaine.butyl methacrylate copolymer singly or in combination with a shellac and a vinyl acetate resin.

8 Claims, 1 Drawing Sheet

TEETH COATING LIQUID

BACKGROUND OF THE INVENTION

(1) Field of the Invention

The present invention relates to a coating liquid for used for tooth or artificial crowns, which colors to white or an optional color, and a teeth beauty applicator.

(2) Description of the Related Art

Teeth beauty coating agents for giving gloss, brightness and whiteness to tooth are known. Disclosed in Japanese Patent Application Laid-Open No. Hei 4-82821 as beauty agents for tooth are a liquid prepared by adding 10 g of water to 90 g of a 50 weight % shellac.ethanol solition, and an even liquid prepared by adding 5 g of a fir tea extract, 5 g of a scale leaf paste, and 10 g of a 0.5% sucrose fatty acid ester aqueous solition to 80 g of a 50 weight % shellac.ethanol solition. Further, disclosed in Japanese Patent Application Laid-Open No. Hei 5-058844 as dental beauty compositions are a liquid prepared by adding 185 g of water to a solition prepared by adding 400 g of a vinyl acetate to 400 g of ethanol and then adding 15 g of an acrylic acid ester copolymer emulsion (11%), and an even liquid prepared by adding 80 g of water, 30 g of an inorganic gelatinizer, and 20 g of a pearl pigment in order to a solition prepared by adding 480 g of a vinyl acetate resin to 360 g of ethanol to disperse them, and further adding 30 g of an acrylic acid ester copolymer emulsion (45%).

However, both of a shellac and a vinyl acetate resin are inferior in a dispersibility of pigments, and in addition, the vinyl acetate resin has a defect that it has inferior water resistance and sticking property and the coated film thereof is liable to peel off. Meanwhile, a shellac has an inferior aging stability, and while pigments stay in a good dispersing state immediately after dispersing them, flocculation and precipitation of the pigments take place at room temperatures after about a week.

Substances having large specific gravities such as titanium oxide, red iron oxide, black iron oxide, and pearl pigments are precipitated as time goes by, and desired is a coating liquid having a so-called redispersibility that the substances once precipitated are dispersed as they used to be without flocculating and turning into solid deposits when they are dispersed again in the liquid.

SUMMARY OF THE INVENTION

The objects of the present invention are to solve the conventional problems described above and to provide a teeth-coating liquid, which is safe for a human body and has an ability to form a coated film having an excellent sticking property and water resistance and which has a good dispersion stability when pigments are contained and can maintain a beautiful gloss over the long period of time after coated on crowns, and a teeth beauty applicator.

A dispersion stability in the present invention means a dispersibility of pigments shown over the long period of time, redispersibility in which while pigments settle down as time goes by, they can easily be dispersed again as they used to be by shaking, or both of these characters.

Investigations repeated by the present inventors in order to solve the problems described above have resulted in finding that an excellent teeth-coating liquid which can solve the preceding problems can be obtained by using an ethanol solution containing a specific copolymer, and coming to complete the present invention.

The teeth-coating liquid of the present invention is characterized in containing an N-methacryloylethyl-N,N-dimethylammonium.α-N-methylcarboxybetaine.butyl methacrylate copolymer and ethanol.

The preferred embodiments include:

(1) a teeth-coating liquid containing 0.1 to 20 weight % of an N-methacryloylethyl-N,N-dimethylammonium.α-N-methylcarboxybetaine.butyl methacrylate copolymer, 5 to 30 weight % of at least one resin selected from the group consisting of a shellac and a vinyl acetate resin, and 10 to 94.8 weight % of ethanol, each based on the whole amount of the coating liquid, and (2) a teeth-coating liquid containing 0.1 to 20 weight % of an N-methacryloylethyl-N,N-dimethylammonium.α-N-methylcarboxybetaine.butyl methacrylate copolymer, 5 to 30 weight % of at least one resin selected from the group consisting of a shellac and a vinyl acetate resin, 1 to 30 weight % of a pigment, and 10 to 94.8 weight % of ethanol, each based on the whole amount of the coating liquid. The preferred pigment includes at least one selected from the group consisting of titanium oxide, an extender pigment and a natural pearl pigment. Titanium oxide having a primary particle diameter of 100 nm or less in terms of an average value is preferred.

The teeth beauty applicator of the present invention comprises a coating liquid-filling tube containing a coating liquid comprising an N-methacryloylethyl-N,N-dimethylammonium.α-N-methylcarboxybetaine.butyl methacrylate copolymer and ethanol, and a coating means disposed at the tip thereof. The applicator has preferably an external constitution comprising a coating means disposed at the tip and a mouth ring for holding the coating member, and a housing connected to the mouth ring, wherein the coating liquid-filling tube described above is installed in the above housing, and the filling tube is connected to the coating means disposed at the tip via a valve and a liquid introducing member.

BRIEF DESCRIPTION OF THE DRAWINGS

FIG. 1 is a cross-sectional drawing of the teeth beauty applicator of the present invention, wherein:

Figure 1:
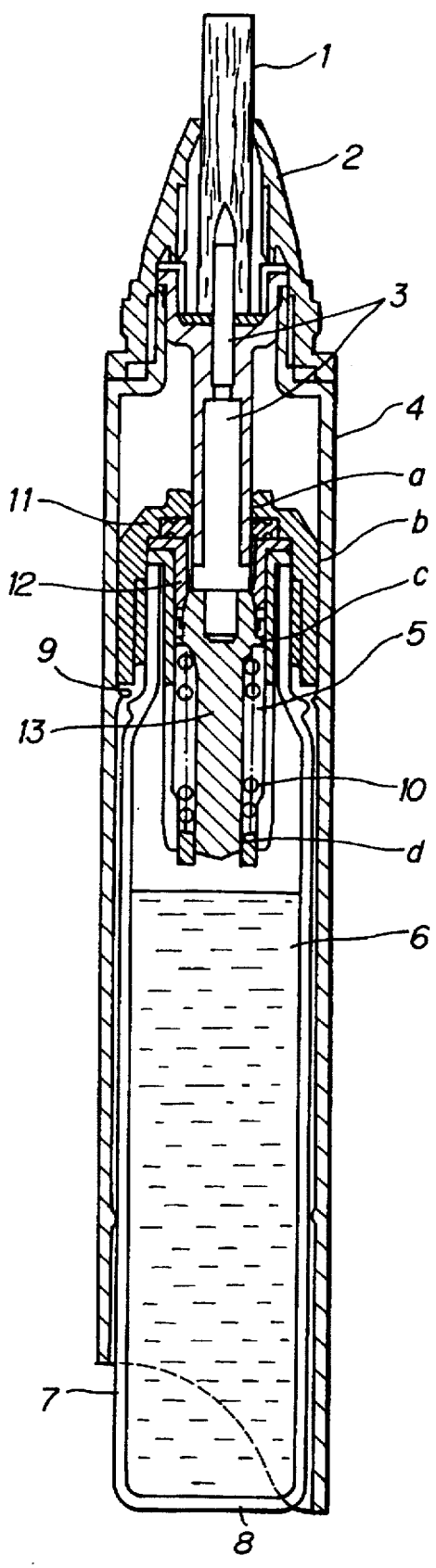

1: coating means (brush),
2: mouth ring (made of a plastic),
3: liquid introducing member,
4: housing,
5: valve,
6: coating liquid,
7: coating liquid-filling tube (inner case),
8: knocking member,
9: stopper,
10: spring in the valve,
11: adapter for the coating liquid-filling tube,
12: valve seat,
13: valve rod,
a, b, c, d: sliding faces.

DETAILED DESCRIPTION OF PREFERRED EMBODIMENTS

The resin used for the teeth-coating liquid of the present invention is an N-methacryloylethyl-N,N-dimethylammonium.α-N-methylcarboxybetaine.butyl methacrylate copolymer, which is an amphoteric ion polymer having a cation group and an anion group in the molecule. Usually, it is used in a form of an anhydrous ethanol solution, and the solution has viscosities of 50 to 200 cps (30° C.) in case of a 30% anhydrous ethanol solution and 500 to 2000 cps (30° C.) in case of a 40% anhydrous ethanol solution (with a Broockfield type viscometer). This copolymer exhibits effects for improving a pigment dispersibility and a coat sticking property. There can be given as the concrete examples thereof, the grade No. "201" and "204" of the 38 to 42% anhydrous ethanol solutions [a viscosity of 500 to 2000 cps measured with the Broockfield type viscometer (30° C.)] and the grade No. "202", "R205", "R205S", and "206" of the 28 to 32% anhydrous ethanol liquids [a viscosity of 50 to 200 cps measured with the Broockfield type viscometer (30° C.)] of Yuka Former AM-75 manufactured by Mitsubishi Chemical Co., Ltd.

The content thereof is 0.01 to 40 weight % based on the whole amount of the coating liquid. Usually, the efficacy as a pigment dispersant, though depending on the kind and amount of the pigment contained in the coating liquid, is revealed in the content of from 0.01% or more. The content of less than 0.01% does not provide a stable dispersion effect or can not disperse a required amount of a pigment. In the case where the above copolymer is added in a large quantity, there are caused the problems that while the water resistance, gloss and redispersibility of a pigment are excellent, an aging stability as a coating liquid is a little inferior, that a coated film gets too thick and is rather liable to peel off from the coated face and that the viscosity becomes high and the coating property is deteriorated. Accordingly, the maximum content is considered to be 40%.

The content in a practical use is 0.1 to 20 weight %. This means that when the liquid is coated on tooth as a brightening agent having a transparency feeling without using pigments, a minimum resin blend amount in which glossiness is confirmed is 0.1%. When a large amount of a pigment is dispersed in a large amount of a resin, involved are the problems that the viscosity is increased and the coating performance is deteriorated and that in addition thereto, the coated film gets thick and is liable to peel off. Accordingly, the content exceeding 20 weight % is not preferred.

The most preferable content falls in a range of 0.1 to 10 weight %. The low content of 1% or less makes the sticking property insufficient but allows the dispersion stability of a pigment to remain good. While the sticking property exceeding those of conventional products can be obtained when the content is 5% or more, the content exceeding about 10%, though depending on the amount of a pigment, deteriorates the coating performance.

Further, the resin used in the present invention can be used in combination with resins such as shellac and a vinyl acetate resin which are conventionally used. The content thereof is 5 to 30 weight % based on the whole amount of a coating liquid. The content of less than 5% does not provide an effect of enhancing the sticking property, and that exceeding 30% markedly deteriorates the coating performance. As described above, the low content of 1% or less makes the sticking property insufficient but allows the dispersion stability of a pigment to remain good. In such case, the combined use with shellac and a vinyl acetate resin can provide a good glossiness and sticking property.

Ethanol is preferably used as a main solvent for the teeth-coating liquid of the present invention, but any solvents may be used as long as they dissolve an N-methacryloylethyl-N,N-dimethylammonium.α-N-methylcarboxybetaine.butyl methacrylate copolymer and have no troubles in a buccal cavity as well as accompanying no unpleasant odor.

Pigments or color components used for the coating liquid of the present invention include inorganic pigments such as carbon black, titan white (titanium oxide) having an average particle diameter of 100 nm or more, titan black, zinc oxide, red iron oxide, chromium oxide, black iron oxide, cobalt blue, alumina white, yellow iron oxide, veridian, zinc sulfide, lithopone, cadmium yellow, vermilion, cadmium red, chrome yellow, molybdade orange, zinc chromate, strontium chromate, white carbon, ultramarine blue, lead white, Prussian blue, mangan violet, aluminum powder, and brass powder, organic pigments such as C. I. 16185, C. I. 45430, C. I. 16255, C. I. 45410, C. I. 45440, C. I. 45100, C. I. 19140, C. I. 15985, C. I. 42053, C. I. 42090, C. I. 73015, C. I. 15850, C. I. 15585, C. I. 15630, C. I. 45170, C. I. 15800, C. I. 15880, C. I. 12120, C. I. 45380, C. I. 26100, C. I. 73360, C. I. 17200, C. I. 12085, C. I. 45370, C. I. 12075, C. I. 21110, C. I. 15510, C. I. 45425, C. I. 45350, C. I. 47005, C. I. 47000, C. I. 21090, C. I. 61570, C. I. 61565, C. I. 59040, C. I. 42095, C. I. 73000, C. I. 42052, C. I. 69825, C. I. 42090, C. I. 20170, C. I. 60725, C. I. 45190, C. I. 15865, C. I. 26105, C. I. 16155, C. I. 16150, C. I. 14700, C. I. 12140, C. I. 15620, C. I. 11725, C. I. 14600, C. I. 12100, C. I. 11680, C. I. 18950, C. I. 10316, C. I. 11380, C. I. 11390, C. I. 13065, C. I. 18820, C. I. 10020, C. I. 42085, C. I. 61520, C. I. 74160, C. I. 60730, and C. I. 20470, and lake pigments which are acid dyes.

The pearl pigment includes scale leaf, various mica titans, sericite, muscovite, pearloyster shell powder, ear shell powder, and button shell powder.

Further, from the viewpoint of the particularity that they are used for tooth, extender pigments having little tinting strength are usually used. The extender pigments include barite powder, precipitated barium sulfate, barium carbonate, calcium carbonate powder, precipitated calcium carbonate, gypsum, asbestos, clay, silica powder, fine silicic acid powder, diatomaceous earth, talc, base magnesium carbonate, alumina white, gloss white, satin white, tricalcium phosphate, and hydroxyapatite. Natural white color having a transparency feeing can be obtained therewith. Among them, hydroxyapatite, tricalcium phosphate, and calcium carbonate are close to the constituent component of a tooth and therefore preferred.

Since titanium oxide is white and has a high masking property, it is an excellent pigment for making tooth look white. Usually used are conventional titanium oxides having a specific gravity of about 4 and a primary average particle diameter of about 200 nm. Of them, fine particulate titanium oxide having a primary average particle diameter of 100 nm or less is preferably used since it is markedly slow in the precipitation speed in a coating liquid and does not generate the problem of precipitation and solidification.

These color components are used in a buccal cavity and therefore safety to a human body has to be sufficiently considered. They should be selected from those approved as food additives and those having a low oral toxicity.

Additives such as surface active agents, perfumes, oil & fats, and hardly volatile hydrocarbons can be added to the teeth-coating liquid of the present invention according to necessity. The use of surface active agents can provide an effect to enhance the physical adhesive strength in an interface between a crown and a coated film and the water resistance and durability against saliva.

Perfumes can provide the effects to mask an unpleasant odor in applying the coating liquid to a buccal cavity and improve a feeling in use. Some of hardly volatile surface active agents, perfumes, oil & fats, and hardly volatile hydrocarbons function also as plasticizers for an N-methacryloylethyl-N,N-dimethylammonium.α-N-methylcarboxybetaine.butyl methacrylate copolymer, shellac and a vinyl acetate resin. This plasticizer effect further improves the sticking property, durability and flexibility of the coated film.

The teeth coating liquid of the present invention is basically prepared by dissolving an N-methacryloylethyl-N,N-dimethylammonium.α-N-methylcarboxybetaine.butyl methacrylate copolymer in ethanol, then adding fine particulate titanium oxide having a primary average particle diameter of 100 nm or less and subjecting the mixture to dispersion treatment with a ball mill, a beads mill, a sand mill, a roll mill, a kneader, a homogenizer, or a supersonic dispersing apparatus to prepare a titanium oxide dispersing liquid, and considering performances as a teeth-coating liquid such as a sticking property and a hue, further adding resins, surface active agents, perfumes, and pigments and the dispersed matter thereof according to necessity. No any problems will be caused by mixing all materials at the same time and subjecting the mixture to dispersing treatment.

The teeth beauty applicator of the present invention comprises a coating liquid-filling tube containing a coating liquid comprising an N-methacryloylethyl-N,N-dimethylammonium.α-N-methylcarboxybetaine.butyl methacrylate copolymer and ethanol, and a coating means disposed at the tip thereof.

A teeth beauty applicator of FIG. 1 can be shown as the concrete example thereof. That is, the external constitution comprises a coating means 1 composed of a brush, a mouth ring 2 made of a plastic for holding the coating member, and a housing 4 connected to the mouth ring. The coating liquid-filling tube 7 described above is installed in this housing 4, and the filling tube is connected to the coating means 1 disposed at the tip via a valve 5 and a liquid introducing member 3.

FIG. 1 shows a condition that the valve 5 is closed. That is, a coating liquid-filling tube-installing member 11 is slided in a direction toward the rear end of the applicator by menas of a spring 10 installed in the valve and stopped with a stopper 9. A knocking member 8 is positioned at the rear end of the applicator. Turning the coating member 1 downward in using the applicator and pushing the knocking member 8 allow the coating liquid-filling tube-installing member 11 to slide forward along the inner wall of the housing 4 and the external wall of the liquid introducing member 3 and cause a valve seat 12 to separate from a valve rod 13 to set the valve to an open state, whereby a coating liquid 6 flows into the coating member 1 via the valve and the liquid introducing member 3 (a, b. C, and d in FIG. 1 show sliding faces, respectively, in sliding).

The teeth-coating liquid of the present invention is excellent in a pigment dispersion stability and a sticking performance and can be filled into a simple applicator. Accordingly, the coating performance is good as well.

EXAMPLES

Next, the present invention will be explained in further detail with reference to examples.

The coating liquids obtained in the examples and comparative examples were used to carry out the following tests.
Test 1: redispersibility test 1 (precipitation test)

A test tube equipped with a sealing cap having a minor diameter of 1 cm is charged with 100 ml of a prescribed coating liquid and left for standing at room temperatures for a month to measure a height of an interface between a supernatant liquid and a precipitate. It was judged that the higher the interface was, the more volume the precipitate had and the better the redispersibility was.
Test 2: redispersibility test 2 (aging practical use test)

The applicator shown in FIG. 1 was charged with the coating liquids obtained in the examples and comparative examples and left for standing for a month while holding it upward. Then, the applicator was shook up and down at a stroke of about 20 cm and a speed of about 1 Hz for about one minute, and lines drawn on a glass plate with the applicator were compared in the hue and density with lines drawn immediately after filling the applicator with the coating liquid to judge visually the difference between the lines drawn separately in the above manners.

⊚: Little change
o: A slight change in hue or density
Δ: A little change in hue or density
×: Extremely thin or incapable of drawing
~: Incapable of drawing from the beginning
Test 3: sticking performance test The coating liquids obtained in the examples and comparative examples were filled into the applicator shown in FIG. 1 and coated on each upper and lower two tooth of twenty monitors to check a change in coated films after 3 hours.

⊚: Little change
o: A little change observed but the coated film remains on the overall face
Δ: Change observed but the coated film remains
×: Coated film hardly or does not at all remain The following coloring liquids were prepared as undiluted liquids for preparing the teeth-coating liquids in the examples and the comparative examples.

Coloring liquid 1:

| | |
|---|---|
| Ethanol | 88% |
| Copolymer "Yuka Former AM75 201" (40% ethanol solution, brand name of Mitsubishi Chemical Co., Ltd.) | 6% |
| Titanium oxide "Titanium Dioxide P25" (average particle diameter 21 nm, manufactured by Degusa Co., Ltd.) | 6% |

The components described above were kneaded with a beads mill for one hour to obtain the coloring liquid 1.

Coloring liquid 2:

| | |
|---|---|
| Ethanol | 13.3% |
| Copolymer "Yuka Former AM75 202" (30% ethanol solution, brand name of Mitsubishi Chemical Co., Ltd.) | 66.7% |
| Titanium oxide "MT-500SA" (average particle diameter 30 to 50 nm, manufactured by Teika Co., Ltd.) | 20% |

The components described above were kneaded with the beads mill for one hour to obtain the coloring liquid 2.

Coloring liquid 3:

| | |
|---|---|
| Ethanol | 49.95% |
| Copolymer "Yuka Former AM75 204" (40% ethanol solution, brand name of Mitsubishi Chemical Co., Ltd.) | 10% |
| Titanium oxide "MT-500B" (average particle diameter 30 to 50 nm, manufactured by Teika Co., Ltd.) | 40% |
| Yellow iron oxide | 0.05% |

The components described above were kneaded with the beads mill for one hour to obtain the coloring liquid 3.

Coloring liquid 4:

| Ethanol | 79.9% |
|---|---|
| Copolymer "Yuka Former AM75 205" (30% ethanol solution, brand name of Mitsubishi Chemical Co., Ltd.) | 10% |
| Titanium oxide "MT-100S" (average particle diameter 50 to 70 nm, manufactured by Teika Co., Ltd.) | 10% |
| Yellow No. 5 Al lake | 0.1% |

The components described above were kneaded with the beads mill for one hour to obtain the coloring liquid 4.

Coloring liquid 5:

| Ethanol | 88% |
|---|---|
| Copolymer "Yuka Former AM75 201" (40% ethanol solution described above) | 6% |
| Titanium oxide "CR-50" (average particle diameter about 250 nm, manufactured by ISHIHARA SANGYO KAISHA, LTD.) | 6% |

The components described above were kneaded with the beads mill for one hour to obtain the coloring liquid 5.

Coloring liquid 6:

| Ethanol | 60% |
|---|---|
| Shellac "transparent white shellac dried product GBN-D" (brand name of Gifu Shellac Mfg. Co., Ltd.) | 20% |
| Titanium oxide "MT-500SA" (the same as described above) | 20% |

The components described above were kneaded with the beads mill for one hour to obtain the coloring liquid 6.

Coloring liquid 7:

| Ethanol | 49.95% |
|---|---|
| Copolymer "Yuka Former AM75 204" (40% ethanol solution described above) | 10% |
| Titanium oxide "CR-50" (the same as described above) | 40% |
| Yellow iron oxide | 0.05% |

The components described above were kneaded with the beads mill for one hour to obtain the coloring liquid 7.

Coloring liquid 8:

| Ethanol | 79.9% |
|---|---|
| Shellac "transparent white shellac dried product Z-GBN" (brand name of Gifu Shellac Mfg. Co., Ltd.) | 10% |
| Titanium oxide "MT-100S" (the same as described above) | 10% |
| Yellow No. 5 Al lake | 0.1% |

The components described above were kneaded with the beads mill for one hour to obtain the coloring liquid 8.

Coloring liquid 9:

| Ethanol | 39.95% |
|---|---|
| Copolymer "Yuka Former AM75 202" (30% ethanol solution described above) | 30% |
| Titanium oxide "CR-50" (the same as described above) | 30% |
| Yellow iron oxide | 0.05% |

The components described above were kneaded with the beads mill for one hour to obtain the coloring liquid 9.

Coloring liquid 10:

| Ethanol | 50% |
|---|---|
| Copolymer "Yuka Former AM75 204" (40% ethanol solution described above) | 10% |
| Extender pigment hydroxyapatite | 40% |

The components described above were kneaded with the beads mill for one hour to obtain the coloring liquid 10.

Coloring liquid 11:

| Ethanol | 88% |
|---|---|
| Shellac "transparent white shellac dried product GBN-D" (the same as described above) | 6% |
| Titanium oxide "CR-50" (the same as described above) | 6% |

The components described above were kneaded with the beads mill for one hour to obtain the coloring liquid 11:

Coloring liquid 12:

| Ethanol | 39.95% |
|---|---|
| Shellac "transparent white shellac dried product GBN-D" (the same as described above) | 30% |
| Titanium oxide "CR-50" (the same as described above) | 30% |
| Yellow iron oxide | 0.05% |

Coloring liquid 13:

| Ethanol | 50% |
|---|---|
| Vinyl acetate resin | 10% |
| Extender pigment hydroxyapatite | 40% |

The components described above were kneaded with the beads mill for one hour to obtain the coloring liquid 13.

EXAMPLE 1

| Ethanol | 80% |
|---|---|
| Coloring liquid 1 | 20% |

The components described above were stirred with a homogenizer for one hour to obtain a teeth-coating liquid.

EXAMPLE 2

| Ethanol | 45% |
|---|---|
| Shellac "transparent white shellac dried product GBN-D" (the same as described above) | 25% |
| Coloring liquid 3 | 28% |
| Natural pearl pigment "Shell Pearl H" (brand name of Kakuhachi Scale Leaf Co., Ltd.) | 2% |

The components described above were stirred with the homogenizer for one hour to obtain a teeth-coating liquid.

EXAMPLE 3

| Ethanol | 60% |
|---|---|
| Vinyl acetate resin | 20% |
| Coloring liquid 2 | 20% |

The components described above were stirred with the homogenizer for one hour to obtain a teeth-coating liquid.

EXAMPLE 4

| Ethanol | 50% |
|---|---|
| Shellac "transparent white shellac dried product "Z-GBN" (the same as described above) | 15% |
| Vinyl acetate resin | 15% |
| Coloring liquid 4 | 20% |

The components described above were stirred with the homogenizer for one hour to obtain a teeth-coating liquid.

COMPARATIVE EXAMPLE 1

| Ethanol | 80% |
|---|---|
| Coloring liquid 5 | 20% |

The components described above were stirred with the homogenizer for one hour to obtain a teeth-coating liquid.

COMPARATIVE EXAMPLE 2

| Ethanol | 45% |
|---|---|
| Shellac "transparent white shellac dried product "GBN-D" (the same as described above) | 25% |
| Coloring liquid 7 | 28% |
| Natural pearl pigment "Shell Pearl H" (brand name of Kakuhachi Scale Leaf Co., Ltd.) | 2% |

The components described above were stirred with the homogenizer for one hour to obtain a teeth-coating liquid.

COMPARATIVE EXAMPLE 3

| Ethanol | 60% |
|---|---|
| Vinyl acetate resin | 20% |
| Coloring liquid 6 | 20% |

The components described above were stirred with the homogenizer for one hour to obtain a teeth-coating liquid.

COMPARATIVE EXAMPLE 4

| Ethanol | 50% |
|---|---|
| Shellac "transparent white shellac dried product "Z-GBN" (the same as described above) | 15% |
| Vinyl acetate resin | 15% |
| Coloring liquid 8 | 20% |

The components described above were stirred with the homogenizer for one hour to obtain a teeth-coating liquid.

The composition ratios of the coating liquids obtained in Examples 1 to 4 and Comparative Examples 1 to 4 are shown in Table 1. The test results of the coating liquids are shown in Table 2.

TABLE 1

(weight %)

| Coating liquid composition | Example 1 | Example 2 | Example 3 | Example 4 | Comparative Example 1 | Comparative Example 2 | Comparative Example 3 | Comparative Example 4 |
|---|---|---|---|---|---|---|---|---|
| Ethanol | 98.32 | 60.946 | 71.998 | 67.38 | 98.32 | 60.946 | 72.000 | 65.98 |
| Resins *1 | | | | | | | | |
| Yuka Former AM75-201 | 0.48 | | | | 0.48 | | | |
| Yuka Former AM75-202 | | | 4.002 | | | | | |
| Yuka Former AM75-204 | | 0.840 | | | | 0.840 | | |
| Yuka Former AM75-R205 | | | | 0.60 | | | | |
| Shellac GBN-D | | 25.000 | | | | 25.000 | 4.000 | |
| Shellac Z-GBN | | | | 15.00 | | | | 17.00 |
| Vinyl acetate resin | | | 20.000 | 15.00 | | | 20.000 | 15.00 |
| Pigments | | | | | | | | |
| Titanium oxide (standard) | | | | | 1.20 | 11.20 | | |
| Titanium oxide (21 nm) | 1.20 | | | | | | | |
| Titanium oxide A (30 to 50 nm) | | | 4.000 | | | | 4.000 | |
| Titanium oxide B (30 to 50 nm) | | 11.200 | | | | | | |
| Titanium oxide (50 to 70 nm) | | | | 2.00 | | | | 2.00 |
| Natural pearl piqment | | 2.000 | | | | 2.000 | | |
| Yellow iron oxide | | 0.014 | | | | 0.014 | | 0.02 |
| Yellow No. 4 Al lake | | | | 0.02 | | | | |
| Total | 100.00 | 100.000 | 100.000 | 100.00 | 100.00 | 100.000 | 100.000 | 100.00 |

*1: in terms of solid content

TABLE 2

|  | Test 1 (cm) | Test 2 | Test 3 |
|---|---|---|---|
| Example 1 | 2.0 | ⊚ | ⊚ |
| Example 2 | 2.5 | ⊚ | ⊚ |
| Example 3 | 2.5 | ⊚ | ○ |
| Example 4 | 2.0 | ⊚ | ⊚ |
| Comp. Example 1 | 1.0 | ○ | ○ |
| Comp. Example 2 | 0.5 | Δ | Δ |
| Comp. Example 3 | 1.0 | ○ | Δ |
| Comp. Example 4 | 0.5 | Δ | Δ |

EXAMPLE 5

| | |
|---|---|
| Ethanol | 63% |
| Shellac "transparent white shellac dried product GBN-D" (the same as described above) | 25% |
| Coloring liquid 1 | 10% |
| Pearl pigment "Timron Supersilk" (mica titan: manufactured by Merck Co., Ltd.) | 2% |

The components described above were stirred with the homogenizer for one hour to obtain a teeth-coating liquid.

EXAMPLE 6

| | |
|---|---|
| Ethanol | 60% |
| Vinyl acetate resin | 20% |
| Coloring liquid 10 | 20% |

The components described above were stirred with the homogenizer for one hour to obtain a teeth-coating liquid.

EXAMPLE 7

| | |
|---|---|
| Ethanol | 55% |
| Copolymer "Yuka Former AM75 202" (30% ethanol solution described above) | 30% |
| Coloring liquid 9 | 10% |
| Natural pearl pigment "Shell Pearl H" (brand name of Kakuhachi Scale Leaf Co., Ltd.) | 5% |

The components described above were stirred with the homogenizer for one hour to obtain a teeth-coating liquid.

EXAMPLE 8

| | |
|---|---|
| Ethanol | 75% |
| Shellac "transparent white shellac dried product "Z-GBN" (the same as described above) | 15% |
| Coloring liquid 4 | 10% |

The components described above were stirred with the homogenizer for one hour to obtain a teeth-coating liquid.

EXAMPLE 9

| | |
|---|---|
| Ethanol | 99% |
| Copolymer "Yuka Former AM75 R205S" (30% ethanol solution; brand name of Mitsubishi Chemical Co., Ltd.) | 0.5% |
| Titanium oxide "CR-50" (the same as described above) | 0.5% |

The components described above were stirred with the homogenizer for one hour to obtain a teeth-coating liquid.

EXAMPLE 10

| | |
|---|---|
| Ethanol | 70% |
| Copolymer "Yuka Former AM75 206" (30% ethanol solution; brand name of Mitsubishi Chemical Co., Ltd.) | 10% |
| Titanium oxide "CR-50" (the same as described above) | 20% |

The components described above were stirred with the homogenizer for one hour to obtain a teeth-coating liquid.

COMPARATIVE EXAMPLE 5

| | |
|---|---|
| Ethanol | 63% |
| Shellac "transparent white shellac dried product GBN-D" (the same as described above) | 25% |
| Coloring liquid 11 | 10% |
| Pearl pigment "Timron Supersilk" (mica titan: manufactured by Merck Co., Ltd.) | 2% |

The components described above were stirred with the homogenizer for one hour to obtain a teeth-coating liquid.

COMPARATIVE EXAMPLE 6

| | |
|---|---|
| Ethanol | 60% |
| Vinyl acetate resin | 20% |
| Coloring liquid 13 | 20% |

The components described above were stirred with the homogenizer for one hour to obtain a teeth-coating liquid.

COMPARATIVE EXAMPLE 7

| | |
|---|---|
| Ethanol | 75% |
| Shellac "transparent white shellac dried product GBN-D" (the same as described above) | 10% |
| Coloring liquid 12 | 10% |
| Natural pearl pigment "Shell Pearl H" (brand name of Kakuhachi Scale Leaf Co., Ltd.) | 5% |

The components described above were stirred with the homogenizer for one hour to obtain a teeth-coating liquid.

COMPARATIVE EXAMPLE 8

| | |
|---|---|
| Ethanol | 75% |
| Shellac "transparent white shellac dried product Z-GBN" (the same as described above) | 15% |
| Coloring liquid 8 | 10% |

The components described above were stirred with the homogenizer for one hour to obtain a teeth-coating liquid.

COMPARATIVE EXAMPLE 9

| | |
|---|---|
| Ethanol | 99% |
| Vinyl acetate resin | 0.5% |
| Titanium oxide "CR-50" (the same as described above) | 0.5% |

The components described above were stirred with the homogenizer for one hour to obtain a teeth-coating liquid.

COMPARATIVE EXAMPLE 10

| | |
|---|---|
| Ethanol | 70% |
| Shellac "transparent white shellac dried product Z-GBN" (the same as described above) | 10% |
| Titanium oxide "CR-50" (the same as described above) | 20% |

The components described above were stirred with the homogenizer for one hour to obtain a teeth-coating liquid.

The composition ratios of the coating liquids obtained in Examples 5 to 10 and Comparative Examples 5 to 10 are shown in Table 3. The test results of the coating liquids are shown in Table 4.

EXAMPLE 11

| | |
|---|---|
| Ethanol | 74% |
| Shellac "transparent white shellac dried product GBN-D" (the same as described above) | 25% |
| Copolymer "Yuka Former AM75-R205S" (30% ethanol solution described above) | 1% |

The components described above were stirred with a magnetic stirrer for one hour to obtain a teeth-coating liquid.

EXAMPLE 12

| | |
|---|---|
| Ethanol | 90% |
| Copolymer "Yuka Former AM75-R205S" (30% ethanol solution described above) | 10% |

TABLE 3

| Coating liquid composition | Example | | | | | | Comparative Example | | | | | (weight %) |
|---|---|---|---|---|---|---|---|---|---|---|---|---|
| | 5 | 6 | 7 | 8 | 9 | 10 | 5 | 6 | 7 | 8 | 9 | 10 |
| Ethanol | 72.16 | 71.20 | 82.095 | 83.69 | 99.35 | 77.00 | 71.80 | 70.00 | 78.995 | 82.99 | 99.00 | 70.00 |
| Resins *1 | | | | | | | | | | | | |
| Yuka Former AM75-201 | 0.24 | | | | | | | | | | | |
| Yuka Former AM75-202 | | | 9.900 | | | | | | | | | |
| Yuka Former AM75-204 | | 0.80 | | | | | | | | | | |
| Yuka Former AM75-R205 | | | | 0.30 | | | | | | | | |
| Yuka Former AM75-R205S | | | | | 0.15 | | | | | | | |
| Yuka Former AM75-R206 | | | | | | 3.00 | | | | | | |
| Shellac GBN-D | 25.00 | | | | | | 25.60 | | 13.000 | | | |
| Shellac Z-GBN | | | | 15.00 | | | | | | 16.00 | | 10.00 |
| Vinyl acetate resin | | 20.00 | | | | | | 22.00 | | | 0.50 | |
| Pigments | | | | | | | | | | | | |
| Titanium oxide | 0.60 | | 3.000 | 1.00 | 0.50 | 20.00 | 0.60 | | 3.000 | 1.00 | 0.50 | 20.00 |
| Mica titan | 2.00 | | | | | | 2.00 | | | | | |
| Natural pearl pigment | | | 5.000 | | | | | | 5.000 | | | |
| Hydroxyapatite | | 8.00 | | | | | | 8.00 | | | | |
| Yellow iron oxide | | | 0.005 | | | | | | 0.005 | | | |
| | | | | 0.01 | | | | | | 0.01 | | |
| Total | 100.00 | 100.00 | 100.000 | 100.00 | 100.00 | 100.00 | 100.00 | 100.00 | 100.000 | 100.00 | 100.00 | 100.00 |

*1: in terms of solid content

TABLE 4

| | Test 1 (cm) | Test 2 | Test 3 |
|---|---|---|---|
| Example 5 | 1.0 | ○ | ○ |
| Example 6 | 1.5 | ○ | Δ |
| Example 7 | 1.5 | ○ | ○ |
| Example 8 | 1.0 | ○ | ○ |
| Example 9 | 1.0 | ○ | ○ |
| Example 10 | 1.0 | Δ | ○ |
| Comp. Example 5 | 0.5 | Δ | Δ |
| Comp. Example 6 | 0.5 | Δ | X |
| Comp. Example 7 | 0.5 | X | X |
| Comp. Example 8 | 0.5 | X | X |
| Comp. Example 9 | <0.5 | X | X |
| Comp. Example 10 | <0.5 | X | X |

The components described above were stirred with the magnetic stirrer for one hour to obtain a teeth-coating liquid.

COMPARATIVE EXAMPLE 11

| | |
|---|---|
| Ethanol | 75% |
| Shellac "transparent white shellac dried product GBN-D" (the same as described above) | 25% |

The components described above were stirred with the magnetic stirrer for one hour to obtain a teeth-coating liquid.

COMPARATIVE EXAMPLE 12

| | |
|---|---|
| Ethanol | 97% |
| Shellac "transparent white shellac dried product GBN-D" (the same as described above) | 3% |

The components described above were stirred with the magnetic stirrer for one hour to obtain a teeth-coating liquid.

The detailed composition ratios of the coating liquids obtained in Examples 11 and 12 and Comparative Examples 11 and 12 are shown in Table 5. The test results of the coating liquids are shown in Table 6.

TABLE 5

| Coating liquid composition | Example 11 | Example 12 | Comparative Example 11 | Comparative Example 12 |
|---|---|---|---|---|
| Ethanol | 74.7 | 97 | 75 | 97 |
| Resins*1 | | | | |
| Yuka Former R205 | 0.3 | 3 | | |
| Shellac GBN-D | 25 | | 25 | 3 |
| Total | 100 | 100 | 100 | 100 |

*1: in terms of solid content

TABLE 6

| | Test 1 (cm) | Test 2 | Test 3 |
|---|---|---|---|
| Example 11 | None | ☉ | ○ |
| Example 12 | None | ☉ | ○ |
| Comp. Example 11 | None | ☉ | Δ |
| Comp. Example 12 | None | ☉ | Δ |

What is claimed is:

1. A teeth-coating liquid comprising 0.1 to 20 weight % of an N-methacryloylethyl-N,N-dimethylammonium.α-N-methylcarboxybetaine.butyl methacrylate copolymer and 10–94.8 weight % ethanol.

2. A teeth-coating liquid as described in claim 1, further comprising any one of a shellac resin and a resin consisting of a shellac and a vinyl acetate.

3. The teeth-coating liquid as described in claim 2, further comprising a pigment.

4. The teeth-coating liquid as described in claim 3, wherein the pigment is at least one selected from the group consisting of titanium oxide, an extender pigment and a natural pearl pigment.

5. A teeth coating liquid comprising 0.1 to 20 percent weight % of an N-methacryloylethyl-N,N-dimethylammonium.α-N-methylcarboxybetaine.butyl methacrylate copolymer, 5 to 30 weight % of any one of a shellac resin and a resin consisting of a shellac and a vinyl acetate resin, and 10 to 94.8 weight % of ethanol, each based on the whole amount of the coating liquid.

6. A teeth-coating liquid comprising 0.1 to 20 weight % of an N-methacryloylethyl-N,N-dimethylammonium.α-N-methylcarboxybetaine.butyl methacrylate copolymer, 5 to 30 weight % of at least one resin selected from the group consisting of a shellac and a vinyl acetate resin, 1 to 30 weight % of a pigment, and 10 to 94.8 weight % of ethanol, each based on the whole amount of the coating liquid.

7. The teeth-coating liquid as described in claim 6, comprising at least titanium oxide as the pigment.

8. The teeth-coating liquid as described in claim 7, wherein the titanium oxide has a primary particle diameter of 100 nm or less in terms of an average value.

* * * * *